United States Patent [19]

McVay

[11] Patent Number: 5,536,254

[45] Date of Patent: * Jul. 16, 1996

[54] LAPAROSCOPIC IRRIGATION BOTTLE PUMP

[75] Inventor: William P. McVay, Doylestown, Pa.

[73] Assignee: Advanced Surgical Products, Inc., Miami, Fla.

[ * ] Notice: The portion of the term of this patent subsequent to Jul. 12, 2011, has been disclaimed.

[21] Appl. No.: 115,068

[22] Filed: Sep. 2, 1993

Related U.S. Application Data

[63] Continuation-in-part of Ser. No. 837,929, Feb. 20, 1992, Pat. No. 5,328,478.

[51] Int. Cl.$^6$ .............................. A61M 5/14; A61M 37/00
[52] U.S. Cl. .............................. 604/147; 604/135
[58] Field of Search .................. 604/30, 31, 35, 604/65–67, 140, 147; 128/DIG. 12, DIG. 13

[56] References Cited

U.S. PATENT DOCUMENTS

| 1,211,304 | 1/1917 | Farr | 604/147 |
|---|---|---|---|
| 2,693,801 | 11/1954 | Foreman | 128/DIG. 12 |
| 3,641,543 | 2/1972 | Rigby | 128/DIG. 13 |
| 3,648,694 | 3/1972 | Mogos et al. | 604/147 |
| 4,029,094 | 6/1977 | Winicki | 128/DIG. 12 |
| 4,117,843 | 10/1978 | Banko | 604/31 |
| 4,332,246 | 6/1982 | Thomson | 128/DIG. 12 |
| 4,872,872 | 10/1989 | Polak | 604/67 |
| 4,913,698 | 4/1990 | Ito et al. | 604/35 |
| 5,019,037 | 5/1991 | Wang et al. | 604/147 |

FOREIGN PATENT DOCUMENTS

| 563176 | 6/1977 | U.S.S.R. | 604/147 |
|---|---|---|---|
| 1496800 | 7/1989 | U.S.S.R. | 604/35 |

*Primary Examiner*—Stephen C. Pellegrino
*Assistant Examiner*—Nancy Mulcare
*Attorney, Agent, or Firm*—Keck, Mahin & Cate

[57] ABSTRACT

A laparoscopic irrigation system and bottle pump for controlling a source of gas pressure driving a source of irrigation solution that includes a monitor for monitoring the source of gas pressure and indicating when the gas pressure falls below a predetermined value. Also, the liquid level of the source of irrigation solution is monitored via infrared radiation and when the level falls to a predetermined value it is detected, a visual and an audible signal is actuated and an alternative source of irrigation solution is selected. Further the level of gas pressure driving the source of irrigation solution is controllable with an electronic circuit containing a stepping motor mechanically connected to a pressure regulator.

10 Claims, 4 Drawing Sheets

LAPAROSCOPIC IRRIGATION BOTTLE PUMP

This application is a continuation-in-part of application Ser. No. 07/837,929 filed Feb. 20, 1992, now Pat. No. 5,328,476.

FIELD OF THE INVENTION

The present invention relates to an improved laparoscopic irrigation bottle pump.

BACKGROUND OF INVENTION

Operative laparoscopy or pelviscopy is the use of a small rigid endoscope called a laparoscope in association with other instrumentation to view the organs of the abdomen via a 10 or 11 mm cannula or tube inserted through the abdominal wall, usually within the umbilicus. Additional puncture sites are created in the abdomen to pass instrumentation used to manipulate, cut, ligate, suture, staple, suction or irrigate a patient's abdominal contents.

A surgical instrument call a laparoscopic suction-irrigation probe (S/I Probe) is used for four functions: 1. blunt dissection, 2. irrigation of abdominal contents, 3. suctioning of smoke, water and debris from the abdominal cavity, and 4. the introduction of additional instrumentation for cutting or ligature. The S/I probe is a thin walled metal tube with a housing on the proximal end incorporating two trumpet valves and an entry port for additional instrumentation. The valves regulate the flow of irrigation solution and vacuum to the probe tip. The probe is connected to a sterile irrigation line which in turn is connected to an irrigation bottle of sterile normal saline or Ringer's solution. These solutions are either supplied in one liter or 1.5 liter semirigid thermoplastic bottles.

In order to push the solution from the bottle into the irrigation line, pressurized carbon dioxide ($CO_2$) gas is introduced into the closed bottle from a laparoscopic irrigation bottle pump. Currently, these irrigation bottle pumps are simply mechanical regulators connected to a toggle valve which allows the user to alternate the liquid flow to a second irrigation bottle when the first bottle becomes empty. The irrigation set incorporates two check valves to prevent the flow from the second bottle emptying into the first bottle and allows the user to exchange the empty bottle for a full one.

However, there are problems with these units. The user, who is usually an operating room nurse, must monitor the liquid level in the bottle so that the toggle valve can be switched at the proper time. If the nurse fails to closely monitor the bottle level, the bottle empties and the $CO_2$ gas will enter the irrigation line. If the line completely fills with gas, the operation is delayed while the irrigation line is purged of gas. This is annoying and time consuming to surgeons and nursing personnel and could be dangerous if too much gas inadvertently enters the abdomen.

A second problem can occur with these irrigation bottle pumps. The source of pressurized gas is usually an "E" size cylinder of $CO_2$, which is 24 to 29 inches tall, between 17 to 18 lbs. in weight and contains about 1240 liters of gas. Because of the nature of carbon dioxide the maximum cylinder pressure is 830 PSI (gage) at 70° F., which is the pressure at which carbon dioxide changes into a liquid state from a gas (known as vapor pressure). If a pressure gauge is used to monitor the amount of gas in the bottle, the pressure will stay at 830 PSI (gage) until all the liquid $CO_2$ in the bottle is exhausted. At this point the bottle contains about 208 liters of gas, which is less than 17% of the original filled volume. From this volume to when the cylinder is empty the pressure gauge drops as gas is used. Therefore, most of the time the cylinder pressure gauge does not budge since the vapor pressure maintains a gauge pressure of 830 PSI. If the gauge is not carefully monitored, the pump can run out of gas and delay the operation until a full cylinder is found and reconnected to the pump. Again, this is annoying and time consuming to nursing personnel.

A third problem can often be seen in these mechanical pumps. Because of backlash within the screw mechanism of manually actuated pressure regulators, the selected pressure often drifts from the desired bottle pressure. The user must then readjust the regulator to compensate for this variance. Sometimes the drift can be as much as ±5 PSI, thus significantly affecting flow to the S/I Probe. Secondly, if a problem should occur within the pressure regulator and allow excessive pressure to build up within the pneumatic circuit, a dangerous condition would occur without a means to prevent or at least warn the user of this condition.

SUMMARY OF INVENTION

To eliminate these problems a laparoscopic irrigation bottle pump has been conceived which electronically monitors and controls the gas head pressure within the irrigation bottle to an operator preset level, detects when an active bottle is nearly empty of irrigation solution, automatically switches to an alternative bottle and alarms the user of the presence of the nearly empty bottle. The pump has the following operating features:

1. A switch or potentiometer means to preset the level of irrigation bottle gas head pressure between 200 and 900 mm HG (gage).
2. A display to indicate the irrigation bottle gas head pressure.
3. Two liquid level sensors which monitor the amount of solution in each bottle and a control circuit which automatically switches the gas head pressure to an alternative bottle when the active bottle is nearly empty of irrigation solution.
4. Visual and audible signals which notify the user to exchange the nearly empty bottle for a full one.
5. Visual and audible signals which caution the user when the CO2 supply cylinder falls below 500 PSI (gage).
6. Electronic monitoring circuits which automatically shutdown the pump if one of the following conditions occurs: a) both irrigation bottles are nearly empty; b) CO2 gas line pressure drops below 25 PSI during use; c) CO2 cylinder pressure is below 500 PSI at power up; and d) bottle pressure exceeds upper and lower safety pressure limits.

DETAILED DESCRIPTION OF PREFERRED EMBODIMENT

Figure 1:
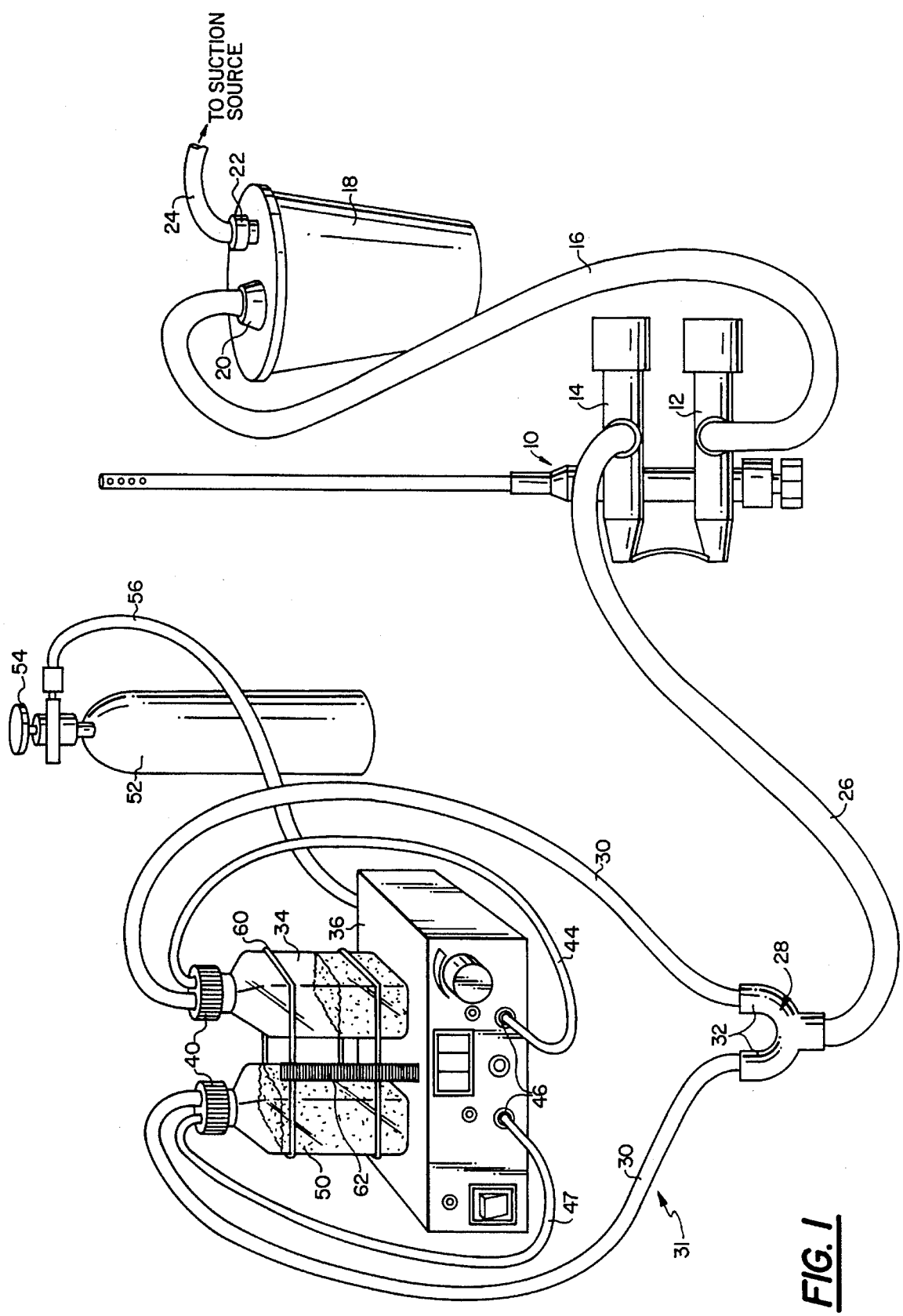
FIG. 1 is a perspective drawing of the novel laparoscopic irrigation pump system according to the present invention.

Referring to the drawings in detail FIG. 1 shows in perspective the novel system. As shown, a known suction-irrigation probe 10 having two trumpet valves 12, 14 is connected by suction tubing 16 leading from valve 12 to a suction cannister 18 via fitting 20. Cannister 18 is connected via fitting 22 and tubing 24 to a suction source (not shown). Tubing 26 leads from valve 14 to a wye branching connection 28. Tubing 30 leads from one branch 32 of connection 28 to an irrigation bottle 34 sitting on top of a housing 36 which contains the pump components. Tubing 30 connects to a fitting 38 which in turn is held in screw cap 40. Fitting 38, see FIG. 3, connects with a draw pipe or tube 42 that extends towards and terminates adjacent the bottom of bottle 34. A gas line 44 is detachably connected via a fitting 46 to housing 36 and leads to a fitting 48 in screw cap 40. A second bottle 50 is located on top of housing 36 spaced from bottle 34 and is connected the same way via gas line 47. A gas cylinder 52 containing $CO_2$ and provided with a shut-off valve 54 feeds high pressure gas via line 56 and an appropriate fitting to housing 36. Thus far all parts and connections are conventional and known.

Figure 3:
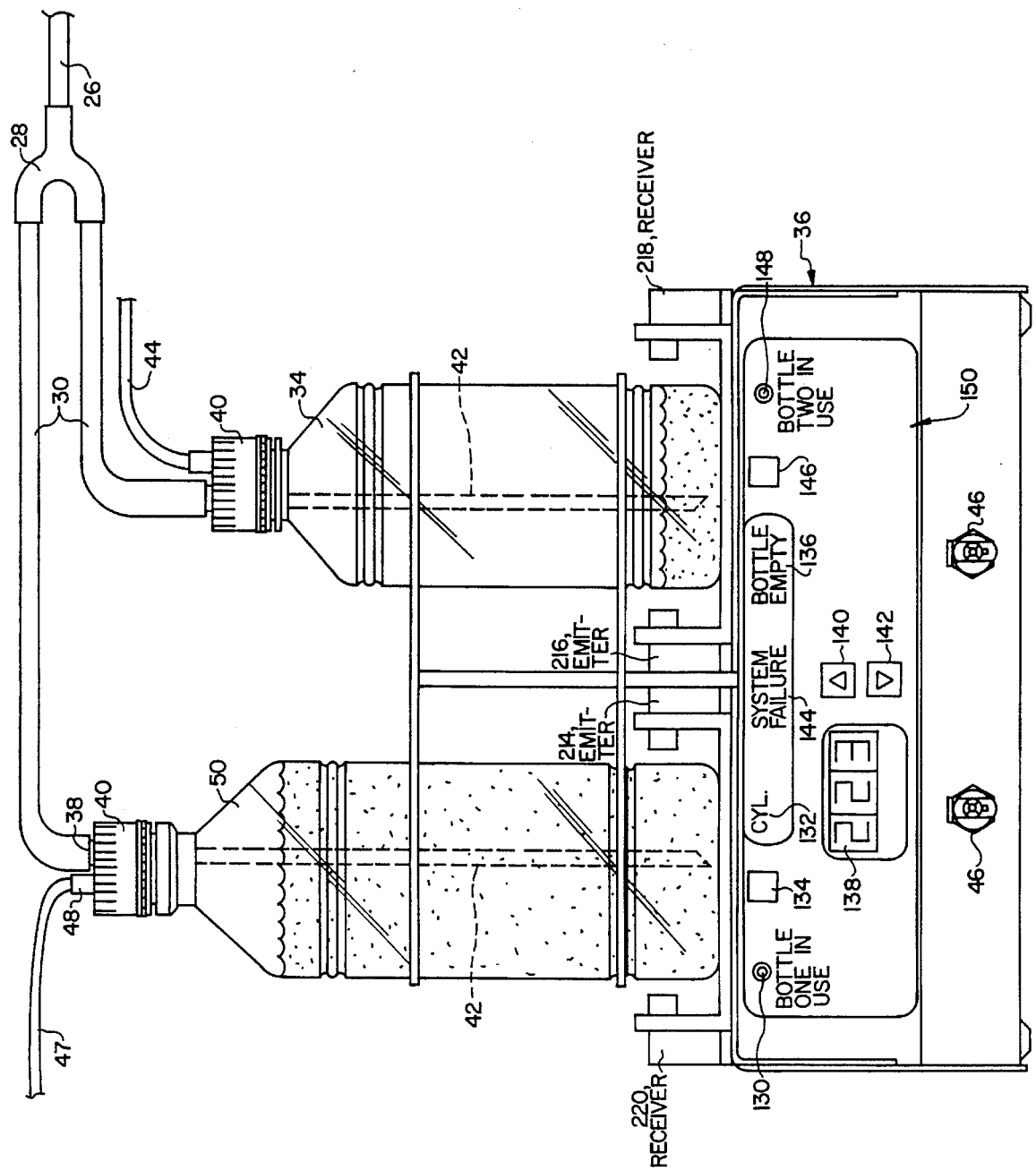
FIG. 3 is a front view of the laparoscopic irrigation pump.

A wire or rod frame 60 attached by posts 62 is mounted to the top of housing 36. A post 62 may have calibration markings on it to give an idea of liquid level in bottles 34, 50. Also, as illustrated in FIG. 3, bottles 34, 50 may be different size, e.g. 1 liter and 1.5 liter irrigation bottles.

Figure 2A:
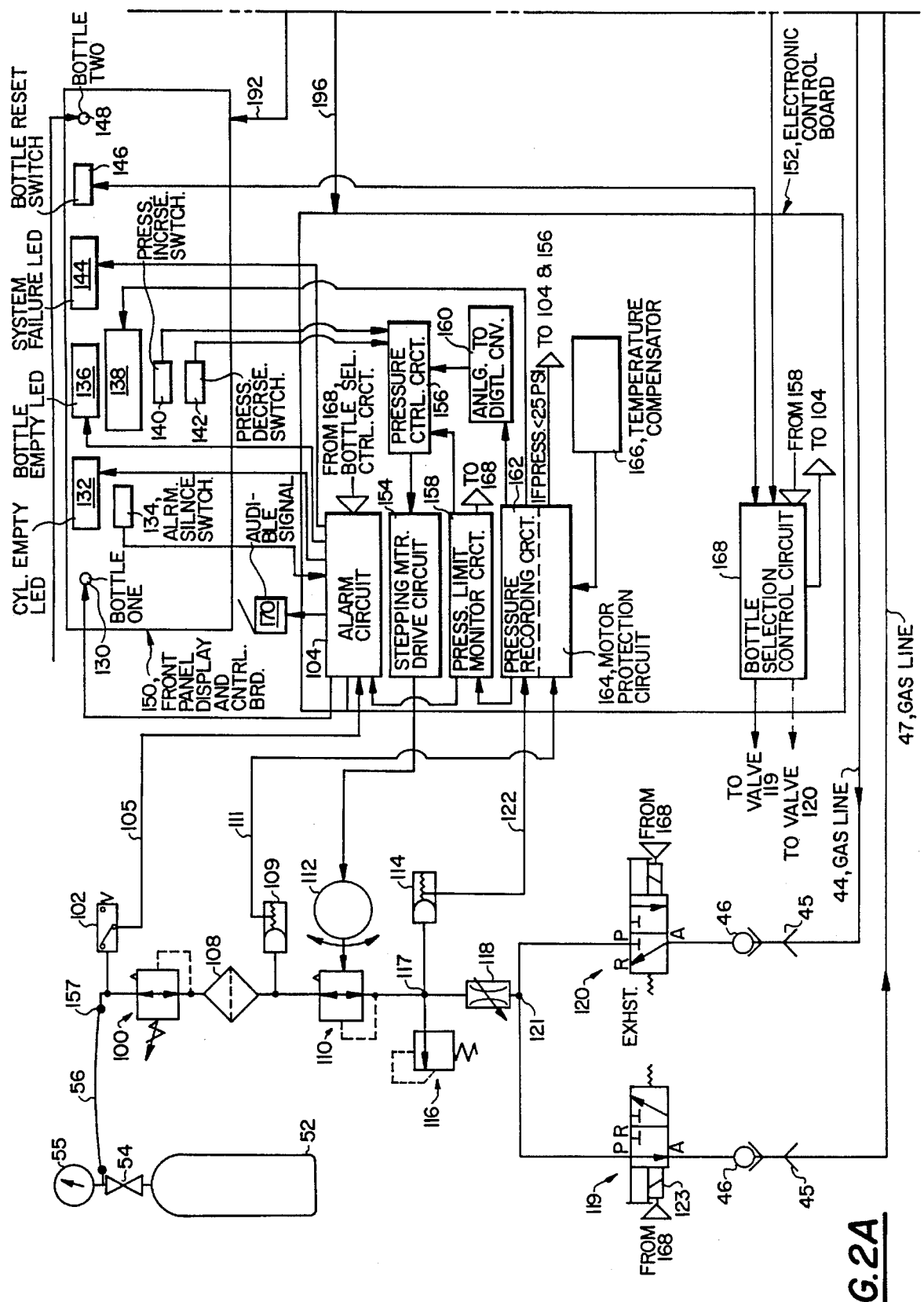
FIG. 2 is a schematic diagram of the pneumatic and electronic circuitry of the system.
Figure 2B:
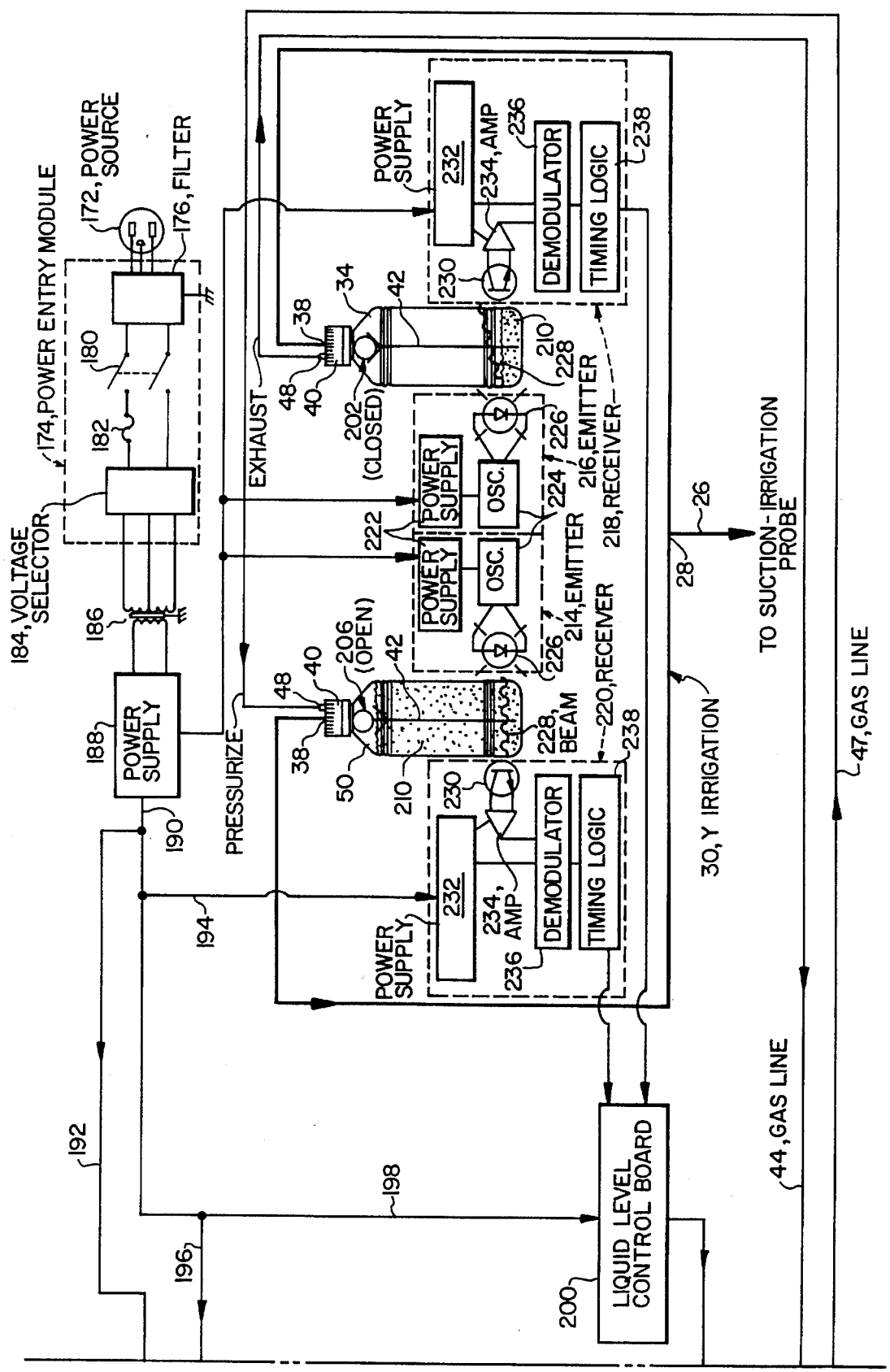

Referring now to FIG. 2, the pneumatic components and gas flow circuit of the system will be described first. A source of high pressure carbon dioxide (CO2) gas (52), such as an E size gas cylinder, is introduced into the pneumatic circuitry via a standard bulkhead gas fitting (157) from a high pressure hose assembly (56). The pressure in the cylinder is monitored by both a standard pressure gauge (55) and a pressure switch (102) which reacts and closes an internal switch when the gas pressure drops below approximately 500 psi. All pressures given herein are gage pressure. When the pressure switch (102) closes, a signal (105) is sent to the alarm circuit (104). An example of pressure switch (102) is a unit that can be obtained from Whitman Controls Corp under model no. J205G-50S-C-12-TB.

The CO2 gas then flows down the inlet line to a cylinder regulator (100) which reduces the gas pressure to a maximum value of 45 psi. This reduction prevents excessive pressure on the downstream pneumatic components. An example of regulator (100) is a unit that can be obtained from Norgren under model no. R83-200-RNLA. The output from the regulator (100) is fed to an particulate filter (108) containing a stainless steel mesh material which removes particulate matter greater than 10 to 15 microns in size from the gas stream thus protecting downstream components from contamination and possible damage. An example of filter (108) is a unit that can be obtained from GP, Inc. identified as model F-4.

Upon exiting the particulate filter (108) the gas flows through a line which tees to a pressure transducer (109) and to a pressure regulator (110) which is controlled by a stepping motor (112). The pressure transducer (109) monitors the gas pressure in the gas line upstream of the pressure regulator (110) and feeds a voltage signal (111) to an electronic circuitry which will explained later. The purpose of monitoring the gas pressure at the upstream side of the pressure regulator (110) is to protect it from possible binding and failure. In general, a pressure transducer produces a D.C. voltage linearly proportional to gas pressure.

The pressure regulator (110) controls the gas pressure in the downstream pneumatic circuitry and irrigation bottles (34) and (50) to within a narrow pressure setting selectable by the user. The pressure regulator (110) is capable of controlling gas pressure to within plus or minus 5 mmHg over a pressure range from 200 mmHg (4 psig) to 900 mmHg (18 psig). Regulator (110) is controlled via voltage step pulses induced into the bipolar stepping motor (112) causing it to rotate a certain number of degrees which axially moves the tip of a valve stem over an orifice thereby altering gas pressure downstream of the regulator. This action either increases or decreases the gas pressure depending on the direction of rotation of the bipolar stepping motor (112).

The CO2 gas next flows into a quad connector (117) to which the following components are connected: pressure transducer (114), pressure relief valve (116), and gas flow control valve (118). The pressure transducer (114) monitors the gas line pressure downstream of the pressure regulator (110) so that a voltage signal (122) is produced for a pressure recording circuit (162). An example of a suitable transducer is model SX30AN from Synsym, Inc.

The relief valve (116) serves as a means for venting gas from the pneumatic circuitry if the gas pressure exceeds a certain level due to mechanical or electrical component failure. Other electronic safety controls are described later which function to prevent excessive gas line pressure but in the event that a component failure should occur, the relief valve (116) will vent gas when gas pressure exceeds a preset amount, e.g. 22 psi. An example of a suitable relief valve can be obtained from Circle Seal Controls, Inc. under model no. 533T1-1M-22.

The gas next flows through a manually settable gas flow control valve (118) which limits the maximum gas flow between 3 and 6 liters per minute at a line pressure of 18 psi. An example of a flow control valve is model GRO-M5 from the Festo Corporation.

The output from the flow control valve (118) is divided by a tee connector (121). Gas flows to a port P on a 3 port, 2 position, normally closed solenoid valve (119) and to an identical solenoid valve (120). When the solenoid (123) is actuated by an electrical voltage, the valve spool is pulled into the solenoid coil. Gas flows into port P and out port A. If the solenoid coil is not actuated as shown in solenoid valve (120), gas is blocked at port P and a spring within the valve housing positions the valve spool so that port A is connected to port R. Any pressure within the gas line (44) connected to port A is therefore exhausted to atmosphere. The solenoid valves are actuated by a bottle selection control circuit (168) which actuates the solenoid valves as required for proper operation. In normal operation each solenoid is activated in sequence with its paired unit. As shown in FIG. 2 irrigation bottle (50) is pressurized through gas line (47). Gas within irrigation bottle (34) is allowed to exhaust back through the gas line (44) to port R in solenoid valve (120). An example of a suitable solenoid valve is model D11-2-3-01 from Dynamco, Inc.

Alternatively, a suitable substitution for the two separate solenoid valves is a spool valve actuated by two solenoids which pull the spool valve to either end of a machined block depending on which solenoid is activated. This action deflects gas flow to an alternative irrigation bottle while exhausting gas from the first irrigation bottle. If no power is provided to the solenoids, springs will center the spool valve which then exhausts both irrigation bottles. Typically, this type of valve is described as a 5 port, 3 position, open center, spring centered, solenoid valve. An example of this unit is model no. W605782417 from the Ross Operating Valve Company.

The gas now flows from the open solenoid valve through one of two bulk head couplers. These couplers are paired female quick connect fittings (46) which accept male quick connect fittings (45). The female fittings are equipped with mechanically opened check valves. The couplers connect the gas lines (44) and (47) from the bottle pump pneumatic circuit to fittings (48) on caps (40) which are tightly screwed onto the irrigation bottles (34) and (50) and seal it from any gas or irrigation solution leakage. An example of a female fitting is one obtainable from Colder Products, Inc. under model no. PMCD16-02-12.

Irrigation bottles (34) and (50) contain standard sterile physiological solutions such as normal saline or Ringer's Solution obtainable from sources such as Baxter-Travenol Laboratories or Abbott Laboratories. The irrigation bottles are usually blow molded from a semirigid thermoplastic material and are produced in sizes of 1.0 and 1.5 liters. Once the gas enters one of the irrigation bottles, it produces a pressure within the head space above the sterile irrigation solution (210) or (212) which drives it up through a flexible draw tube (42). The draw tubes (42) are made from flexible PVC tubing which are made long enough for 1.5 liter irrigation bottles but bend for the shorter 1.0 liter bottles.

The tube (42) is in turn connected to a normally closed check valve cartridge (202) and (206). The pressure forces open the check valve and allows irrigation solution to flow to one leg of the Y-irrigation set (31). The purpose of the check valve cartridges (202) and (206) is to prevent sterile solution from entering an empty irrigation bottle from a full one once gas is exhausted from the empty bottle. The solution flow is directed away from the irrigation bottles and not from one bottle to the other-since back flow or pressure from any liquid automatically closes a check valve.

The wye irrigation set (31) is made from ¼" ID×⅜" OD flexible plastic tubing made from polyvinyl chloride resin. The wye irrigation set consists of tubing (26) which connects a laparoscopic S/I probe (10) to a Y connector (28). Each leg (32) of the Y connector mates to tubing (30) which connects to fitting (48) on each bottle cap (40). Irrigation solution is metered into the patient's abdomen with the manually operated irrigation valve (14) located on the body of the S/I probe. The surgeon simply opens the valve (14) to produce an irrigation solution flow.

Electrical power to the pump is obtained from the mains via a grounded plug (172) and feeds through a power entry module (174). The module consists of a radio frequency interference filter (176) connected to a power switch (180) which is in turn connected to a fuse (182). The power feeds through a voltage selector (184), which allows the use of either 110 volt, 60 Hz power or 220 volt, 50 Hz power depending how the input lines are configured to an isolation transformer (186). An example of a suitable power entry module is obtained from Corcom, Inc under model 5EHM4S. Electrical power then feeds through the isolation transformer (186) and into a DC power supply (188) which converts alternating current to direct current of both 5 and 12 volts amplitude. DC power is fed by lines (190,192, 194, 196, 198) to components on an electronic control board (152), liquid level control board (200), front panel display and control board (150), a pair of infrared light emitters (214) and (216), and a pair of infrared light receivers (218) and (220).

The electronic control board (152) and front panel display and control board (150) will now be explained. Generally, standard electronic components and digital relay logic components such as AND, OR, NOR and NAND gates are used within the circuitry to produce the desired switching and logic sequencing. The alarm circuit (104) accepts a signal (105) from the pressure switch (102) when it closes around 500 psi. This circuit then turns on a LED indicator (132), marked "Cylinder Empty". Simultaneously, the alarm circuit (104) turns on an audible signal (170). This can take the form of a piezoelectric buzzer or bell which is turned off and reset with a momentary pushbutton (134) on the front panel board (150). However, the LED indicator will stay lit until the pressure switch (102) is reset when the nearly empty gas cylinder (52) is exchanged for a full one. Since a full cylinder contains approximately 830 psi, the pressure switch will open and eliminate the signal to the alarm circuit (104).

The voltage signal (122) from the pressure transducer (114) is amplified through a pressure recording circuit (162) which corrects the voltage signal for temperature changes using well known temperature compensator circuit means (166). The corrected signal from circuit (162) is converted to a digital signal with an analog to digital conversion circuit (160) which in turn sends a series of digital pulses of a certain amplitude to a pressure control circuit (156). A stepping motor drive circuit (154) accepts pulse signals from the pressure control circuit (156). If the user wishes to increase the pressure with the irrigation bottle, a "Pressure Increase" switch (140) located on the front panel display and control board (150) is activated to increase a reference voltage level within the pressure control circuit (156). Circuit (156) compares the actual voltage to the reference voltage. Since the voltage difference is positive, it sends a positive signal to the motor drive circuit (154). Circuit (154) then turns on stepping motor (112), which due its direct mechanical connection to the pressure regulator (110), operates to increase the pressure within the pneumatic circuit. As the gas line pressure increases, the voltage difference between the desired and measured voltages within the pressure control circuit (156) is reduced until eventually the voltage difference is zero and the stepping motor (112) stops. Conversely, if the user wishes to decrease the pressure within the pneumatic circuit a "Pressure Decrease" switch (142) is activated. This action decreases the reference voltage level within circuit (156) which sends a negative voltage signal to the stepping motor drive circuit (154). This circuit reverses the direction of the stepping motor (112) which causes the pressure regulator (110) to decrease the measured pressure within the pneumatic circuit until the voltage difference shrinks to zero and the stepping motor (112) stops.

Alternatively, a manually adjustable pressure selection potentiometer can be substituted for the two switches. The potentiometer increases or decreases the reference voltage level depending on the direction of knob rotation.

The pressure recording circuit (162) also sends a signal to a 3½ segment bottle pressure digital display (138) so that the measured pneumatic circuit gas pressure is shown to the user on the front panel in mmHg. The operator therefore has feedback on the exact pressure within the irrigation bottles. Alternatively, an analog pressure gauge could be substituted for a electronic digital display to show the operator the gas pressure within the system.

In order to prevent damage to the stepping motor (112) or its mating pressure regulator (110), a motor protection circuit (164) monitors a voltage signal (111) from the pressure transducer (109). This circuit is necessary since low gas pressure causes the pressure control circuit to turn on the stepping motor continuously, which may bind the pressure regulator and potentially burn out the stepping motor. In order to prevent this event, if the voltage signal (111) drops to a value corresponding to a gas pressure of 25 psi, the motor protection circuit (164) sends a signal to the alarm circuit (104) which switches on the system failure LED (144) and the audible signal (170). Simultaneously, the circuit sends a signal to pressure control circuit (156) which stops the stepping motor (112). The pump is effectively shutdown until the gas pressure is increased by usually exchanging a nearly empty gas cylinder for a full one.

In order to prevent gas line pressure which is outside the acceptable operating range of the pump, a pressure limit monitor circuit (158) compares the voltage generated from the pressure recording circuit (162) to reference voltages corresponding to upper and lower operating pressure limits. Once these operating pressure limits are reached, a signal is sent to the pressure control circuit (156) which stops the stepping motor (112) as explained above. Thus, the operator normally will not be able to exceed the lower (200 mm Hg) or upper (900 mm Hg) operating pressure limits.

In order to provide an electronic safety feature, the pressure limit monitor circuit (158) compares the voltage generated from the pressure recording circuit (162) to reference voltages corresponding to upper and lower safety pressure limits and, if exceeded, the alarm circuit (104) turns on a system failure LED (144) and audible signal (170).

Simultaneously, the pressure limit monitor circuit (158) also sends a signal to the bottle selection control circuit (168) which deactivates both solenoid valves (119) and (120), which exhaust gas from both infusion containers (34) and (50). The upper safety pressure limit is set at 20 psi (1000 mm HG) and the lower safety pressure limit is set at 3 psi (150 mm HG).

Bottle selection control circuit (168) is a logic control circuit which accepts input from the liquid level control board (200) and sends signals to the solenoid coils on solenoid valves (119) and (120) as well as to the alarm circuit (104). It also accepts input from the pressure limit monitor circuit (158). The logic diagram for circuit (38) is as follows:

| Irrigation Bottle Status | Infrared Receiver Signal Status 218 | 220 | Signal to Solenoid Valve |
|---|---|---|---|
| 34 & 50 Full | + | + | 120 |
| 34 Full, 50 Empty | + | − | 120 |
| 34 Empty, 50 Full | − | + | 119 |
| 34 & 50 Empty | − | − | None |
| Signal from Pressure | any condition | | None |

The bottle selection control circuit (168) sends a signal to the alarm circuit (104) whenever an empty irrigation bottle is detected by an infrared receiver (218) or (220). The alarm circuit (104) responds by sending a signal to the "Bottle Empty" LED (136) and to the audible signal (170), which notifies the user to change the empty bottle. Simultaneously, the alarm circuit (104) turns off the corresponding "bottle in use" LED under the empty bottle and turns on the alternative "bottle in use" LED if the alternative irrigation bottle is full. As shown in FIG. 2 since the irrigation bottle (50) is full, the liquid level control circuit (200) sends a signal to the bottle selection circuit (168) which in turn activates the solenoid valve (119). Bottle selection control circuit (168) sends a signal to the alarm circuit (104) which turns on "bottle one in use" LED (130). Since the irrigation bottle (34) is nearly empty, the liquid level control circuit (200) has latched open and does not produce a signal for bottle selection control circuit (168), which in turn deactivates solenoid valve (120). Circuit (168) also signals the alarm circuit (104) which turns off "bottle two in use" LED (148) and activates the "bottle empty" LED (136) and the audible signal (170).

If both bottles are nearly empty, the bottle selection control circuit (168) does not activate either solenoid valve (119) or (120). The pump is effectively shutdown until the user substitutes an empty bottle for a full one and activates the bottle reset switch (146).

The user silences the audible alarm by depressing alarm silence switch (134), exchanges the empty bottle (34) for a full one and depresses the bottle reset switch (146). This action turns off the "bottle empty" LED (136) which allows the bottle selection control circuit (168) to switch to irrigation bottle (34) whenever bottle (50) becomes empty.

The liquid level sensor and control system is now explained. An infrared light receiver (218) or (220) noninvasively measures the presence of sterile solution in an irrigation bottle and provide a voltage signal to a liquid level control board (200), which is a digital latching switching circuit producing a signal in turn for the bottle selection control circuit (168). Normally, the liquid level control board (200) sends a signal to circuit (168) if irrigation solution level is above the infrared receiver (220). This level is adjustable but is usually set at about 1 inch from the bottom of the bottle.

An infrared light emitter (214) or (216) produce a narrow beam of modulated infrared light (228) which is transmitted through the plastic walls of the irrigation bottle (34) or (50) and transparent sterile solution (210) or (212). Once the irrigation solution (210) level drops to height of the transmitted beam (228), the meniscus, which is formed by the contact of the top surface of the irrigation solution (210) with the walls of the bottle (34), acts as a lens and deflects the transmitted beam (228) at an angle which is out of alignment with the opposing infrared receiver (218). The infrared receiver momentarily loses sight of the beam and fails to send a signal to the liquid level control board (200). The liquid level control board (200) senses this signal loss, latches to an open circuit mode and consequently does not send a signal to the bottle selection control circuit (168). The infrared emitter and receiver can sense the location of the meniscus even if the sensors are not in contact with the irrigation bottles or the walls of the bottles are slightly warped or bent by the internal gas pressure.

The infrared light emitter (214) or (216) consists of a regulated power supply (222) which in turn drives an oscillator (224) which produces a modulated infrared light beam from an infrared light emitting diode (LED) (226). The infrared receiver (218) or (220) consists of a photo detector (230) which produces a voltage as a function of the light hitting the photo detector. The voltage is increased to a usable level by an amplifier (234) which is powered by a regulated power supply (232). The signal is demodulated by a circuit (236) and the pulse timing is sensed by a timing logic circuit (238). The signal is in turn sent to the liquid level control board (200).

As an alternative to an infrared light emitter and detector pair, an ultrasonic transducer can be used to sense the presence of liquid within the irrigation bottle. Associated electronics generate an ultrasonic burst of energy at the ultrasonic transducer. This ultrasonic energy burst is transmitted across the walls and irrigation solution of the irrigation bottle and is partially reflected back to the transducer after a period of time has elapsed, which is usually less than 500 milliseconds. The transducer which now waits for the reflected signal produces a voltage spike upon the return of the reflected ultrasonic signal. This voltage spike is sensed by associated electronics and processed further. If irrigation solution level is above the transducer, the ultrasonic signal is received within the expected time frame built within the associated electronics. The presence of air between the bottle walls slows the reflected ultrasonic signal velocity so that the voltage spike is not received within the expected time frame. Upon loss of a timely reflected ultrasonic signal, an output voltage is generated within the associated electronics, which indicates the presence of a low liquid level. An open collector circuit is connected to the associated electronics to detect the output voltage which in turn produces a signal for the bottle selection control circuit (168) as described above. Although an ultrasonic transducer measures the actual level of irrigation solution within the bottle, the transducer must be in firm contact with the walls of the bottle so that the ultrasonic energy is properly transmitted and received. The shape of the irrigation bottle influences the reflected ultrasonic signal strength. The bottle shape for various pressures is not always predictable or consistent but is usable for more rigid and opaque irrigation bottles.

Although the invention has been described in terms of a preferred embodiment, changes are possible which do not depart from the spirit of the invention. Such changes fall within the purview of the invention as claimed.

What is claimed is:

1. A laparoscopic irrigation pump for controlling gas under pressure driving irrigation solution from a container comprising:

first means for monitoring a source of gas under pressure and responsive to the gas pressure falling below a predetermined value to indicate same, second means for introducing gas under pressure into a container containing irrigation solution for driving the irrigation solution out of the container, third means for monitoring liquid level of irrigation solution in the container, detecting when the level falls to a predetermined value and responsive thereto terminating flow of the irrigation solution out of the container, and fourth means for receiving gas under pressure from the source, delivering gas via said second means to the container and controlling the level of gas pressure delivered via said second means to the container for driving the irrigation solution out of the container, said fourth means including a pressure regulator for acting on gas from the source to adjust the gas pressure to a predetermined level, a pressure transducer for sensing positive and negative deviations of gas pressure on the output side of the pressure regulator correlated with said predetermined level of gas pressure and for converting same into corresponding electrical signals, control means acting responsive to said electric signals for controlling the pressure regulator to maintain said predetermined level of gas pressure.

2. A pump according to claim 1, further including a manually settable control for setting the predetermined level of gas pressure and further control means for acting responsive to said manually settable control for controlling said stepping motor to adjust the pressure regulator.

3. A pump according to claim 2 wherein a stepping motor effects the adjustment of the pressure regulator.

4. A pump according to claim 2 wherein the pressure regulator of the fourth means controls the gas from the source to adjust the gas pressure to from about 200 to about 900 mm Hg (gage).

5. A pump according to claim 1 wherein the indications are visual.

6. A pump according to claim 1 wherein the indications are audible.

7. A pump according to claim 1 further including a display of the gas pressure.

8. A pump according to claim 1 wherein a plurality of containers of irrigation solution are provided and said third means switches the gas pressure from one containers of irrigation solution to another responsive to said second means.

9. A pump according to claim 1 wherein said fourth means includes temperature compensation means for sensing ambient temperature and for correcting the corresponding electrical signals for temperature changes.

10. A laparoscopic irrigation system comprising:

a) a source of gas pressure, b) a valved irrigation probe, c) a source of irrigation solution, d) first means for transferring irrigation solution from the source of irrigation solution to the probe, e) second means for transferring gas pressure from the source of gas pressure to the source of irrigation solution to drive the solution to the probe when its valve is actuated, f) control means coacting with said second means for monitoring the gas pressure and indicating when pressure falls below a predetermined value, coating with the source of irrigation solution for monitoring via infrared radiation the source of irrigation solution and indicating when the level of the solution falls to a predetermined level and coacting with said second means for controlling the level of gas pressure being transferred from the source of gas pressure to the source of irrigation solutions, wherein a plurality of sources of irrigation solution are provided and each of said plurality of sources of irrigation solution are provided with a said first means and a said second means for transferring irrigation solution and gas pressure, respectively, and valve means are included in the control means for selecting one of said plurality of sources of irrigation solution to supply the irrigation solution to said probe and for switching gas pressure to another of the plurality of sources of irrigation solution when the level of solution in the selected source of irrigation solution falls to the predetermined level and further includes valve actuation means for actuating said valve means responsive to a signal from said control means generated when the infrared monitoring indicates that the level of solution in the selected source of irrigation solution has fell to said predetermined level.

\* \* \* \* \*